United States Patent [19]
van den Honert

[11] Patent Number: 4,856,525
[45] Date of Patent: Aug. 15, 1989

[54] MULTICHANNEL ELECTRICAL STIMULATOR WITH IMPROVED CHANNEL ISOLATION

[75] Inventor: Christopher van den Honert, St. Paul, Minn.

[73] Assignee: Minnesota Mining and Manufacturing Company, St. Paul, Minn.

[21] Appl. No.: 158,089

[22] Filed: Feb. 16, 1988

Related U.S. Application Data

[63] Continuation of Ser. No. 786,193, Oct. 10, 1985, abandoned.

[51] Int. Cl.$^4$ .............................................. A61N 1/04
[52] U.S. Cl. .................................................. 128/421
[58] Field of Search ........ 128/419 PG, 419 E, 419 R, 128/420–423, 783, 798, 799, 908

[56] References Cited

U.S. PATENT DOCUMENTS

| | | | |
|---|---|---|---|
| 3,055,372 | 9/1962 | Browner | 128/421 |
| 3,727,616 | 4/1973 | Lenzkes | 128/419 E |
| 3,814,106 | 6/1974 | Berkovits | 128/419 PG |
| 3,848,608 | 11/1974 | Leonard | 128/799 |
| 3,915,154 | 10/1975 | Cosentino | 128/908 |
| 4,019,518 | 4/1977 | Maurer et al. | 128/419 R |
| 4,390,756 | 6/1983 | Hoffmann et al. | 128/419 R |
| 4,470,418 | 9/1984 | Herscovici et al. | 128/419 PG |

FOREIGN PATENT DOCUMENTS

| | | | |
|---|---|---|---|
| 3415830 | 10/1985 | Fed. Rep. of Germany | 128/422 |
| 2493154 | 5/1982 | France | 128/422 |
| 1248799 | 10/1971 | United Kingdom | 128/422 |
| 1418293 | 12/1975 | United Kingdom | 128/422 |
| 2129308 | 5/1984 | United Kingdom | 128/422 |

OTHER PUBLICATIONS

White et al, Study of Transdermal Electronics for an Auditory Prosthesis, 8th Quarterly Progress Report, Feb. 1, 1983 through Apr. 30, 1983, NIH Contract No. N01-NS-1-2354, Stanford Electronics Laboratory, Stanford University, Stanford, Calif., 94305.

*Primary Examiner*—Francis Jaworski
*Attorney, Agent, or Firm*—Donald M. Sell; Walter N. Kirn; William D. Bauer

[57] ABSTRACT

An electrical stimulator having a plurality of channels adapted to stimulate bodily tissue with an electrical current on each of the plurality of channels. First and second electrodes are coupled to each of the plurality of channels and adapted to be coupled to the bodily tissue for passing electrical current through the bodily tissue. A first current source and a second current source is supplied for each of the plurality of channels. The first current source being coupled to the first electrode and the second current source being coupled to the second electrode. First and second current sources operate in concert. The value of the current supplied being equal in magnitude and being oppositely oriented for each of the first and second current sources for each of the plurality of channels at any given instant of time. In one embodiment, one of the current sources for one of the electrodes in one of the plurality of channels may be eliminated.

4 Claims, 3 Drawing Sheets

MULTICHANNEL ELECTRICAL STIMULATOR WITH IMPROVED CHANNEL ISOLATION

BACKGROUND OF THE INVENTION

This is a continuation of application Ser. No. 786,193 filed Oct. 10, 1985, and now abandoned.

BACKGROUND OF THE INVENTION

The present invention relates to an electrical stimulator adapted to stimulate bodily tissue and more particularly to an electrical stimulator having a plurality of stimulation channels adapted to stimulate bodily tissue.

Electrical stimulators adapted to stimulate bodily tissue are well known. Examples of such electrical stimulators include cochlear implants and transcutaneous electrical nerve stimulators. A cochlear implant supplies an electrical current to electrically stimulate the auditory nerve in order to simulate hearing in an otherwise deaf individual. Transcutaneous electrical nerve stimulators (TENS) are utilized for pain control or for controlled muscle activation. In both the cochlear implant and the TENS stimulators, a pair of electrodes are attached to the bodily tissue to be stimulated. Electrical current is then supplied to this electrode pair to provide a stimulation current between the electrodes which passes through the bodily tissue to be stimulated. This electrical current in the bodily tissue stimulates the appropriate nerves, i.e., the auditory nerve for the cochlear implant and pain bearing nerves for the TENS, to achieve the desired function, i.e., simulated hearing or alleviation of pain, respectively.

In certain situations, it is desirable to have an electrical stimulator which has a plurality of channels. The plurality of channels may be designed to provide more than one type of information to the bodily tissue to be stimulated. With a cochlear implant, a plurality of channels may supply different types of information. As an example, one channel may provide information about a specific frequency range and a second channel may provide information about a different frequency range. This type of cochlear implant is designed to take advantage of the frequency place value relative to a position within the cochlea. As an example, a TENS stimulator may control different nerves and hence different muscles with different channels.

Usually the theory of operation of such multichannel electrical stimulators is that each channel of the stimulator is completely independent of the others. In practice this may not be the case. The effectiveness of multichannel operation of electrical stimulators is impeded by diversion of current intended to pass between electrodes of one electrode pair to the electrode or electrodes of another electrode pair. Electrical current which is intended to pass between one electrode pair may be diverted to another electrode pair by the conduction of the bodily tissue. In general, attempts to control the interaction between the electrode pairs is accomplished by the physical spacing of the electrode pairs. However, spacing between electrode pairs cannot always be controlled. With a cochlear implant, for example, pairs of electrodes must be rather closely spaced to enable placement of more than one electrode pair within the cochlea.

In essence, the effect is that a plurality of channels of stimulation in an electrical stimulator are not completely isolated from each other. That is, the stimulation of one electrode pair has an effect upon the stimulation of another electrode pair. Thus, less than ideal multichannel operation is achieved. The theoretical result of multichannel stimulation is significantly compromised.

Another mechanism which has been used be achieve the isolation of multiple channels in a multichannel stimulator is to electrically isolate the output stages of the stimulator. This, however, requires rather complex circuitry, with attendant increased cost and decreased reliability, and, in the case where the current is being inductively coupled from external transmitter to an implanted electrode pair as in a typical cochlear implant, a plurality of receiving coils.

SUMMARY OF THE INVENTION

The present invention significantly reduces the detrimental interaction of one channel of the electrical stimulator by another channel of the electrical stimulator.

In a conventional electrical stimulator, each channel has a current source which drives current between one electrode and electrical ground, which be common to electrodes of multiple channels. However, a single current source for each channel requires only that the current in the loop containing the electrode and electrical ground be equal to the value of the current source and not necessarily that the current passing to ground pass through any particular one of electrodes coupled to electrical ground. If the electrical power supplies of the channels of the electrical stimulator are not electrically isolated, i.e., if two or more electrodes are connected to the same electrical ground, a cross current from one electrode pair to another electrode pair could occur while still maintaining the loop current requirements of the single current source (for each channel).

The present invention provides improved channel isolation without requiring electrically isolated power supplies. Each channel of the electrical stimulator has a pair of electrodes. Each channel of the electrical stimulator has a pair of current sources (in one embodiment one channel may have a single current source) which work in concert with each other. One current source is coupled to each electrode of the electrode pair. The current sources operate harmoniously, i.e., when one current source is sourcing (or sinking) a certain current (at a given instant of time) its complementary current source is sinking (or sourcing) a substantially identical current in magnitude to certain current. This being the case, the current passing between the electrode pair is substantially equal to the desired amount of current. Current leak between electrode pairs is minimized and channel isolation is significantly improved.

In one embodiment, one electrode may be left without a separate current source. If all other electrodes sink/source the proper amount of current, the only current left for the final electrode is the proper amount, thus, one current source may be saved. In this embodiment, for a two channel electrical stimulator, three current sources for the four electrodes (two electrode pairs) would be required. Similarly, for a three channel electrical stimulator, five current sources for six electrodes (three electrode pairs) would be required.

In summary, the present invention provides an electrical stimulator having a plurality of channels having an electrical common. The stimulator is adapted to stimulate bodily tissue with an electrical current on each of the plurality of channels. A first electrode and a second electrode for each of the plurality of channels are provided. The first electrode and the second electrode are adapted to be coupled to the bodily tissue for passing the electrical current through the tissue between the first electrode and the second electrode. A first current source and a second current source for each of the plurality of channels are provided. The first current source is coupled between electrical common and the first electrode. The second current source is coupled between the second electrode and the electrical common. The first current source is substantially equal in magnitude to the second current source and is oppositely oriented for each of the plurality of channels at a given instant of time. Constructed in this manner the first electrode and the second electrode source and/or sink substantially identical currents, thus, achieving significantly improved isolation of stimuli between the plurality of channels.

In one embodiment of the present invention, an electrical stimulator is provided having a plurality of channels having an electrical common. The stimulator is adapted to stimulate tissue with an electrical current on each of the plurality of channels. A first electrode and a second electrode for each of the plurality of channels are provided. The first electrode and the second electrode are adapted to be coupled to the tissue for passing the electrical current through the tissue between the first electrode and the second electrode. A first current source and a second current source for all but one of the plurality of channels are provided. The first current source is coupled between electrical common and the first electrode and the second current source are coupled between the second electrode and the electrical common. At a given instant of time and for each of all but one of the plurality of channels, the first current source is substantially equal in magnitude to the second current source and is oppositely oriented. The electrical stimulator also provides a current source for the one remaining of the plurality of channels being coupled between the electrical common and the first electrode and the second electrode being coupled directly to electrical common. Constructed in this manner the first electrode and the second electrode sink and/or source substantially identical currents achieving significantly improved isolation of stimulus between the plurality of channels.

BRIEF DESCRIPTION OF THE DRAWINGS

The foregoing advantages, construction and operation of the present invention will become more readily apparent from the following description and accompanying drawings in which.

DETAILED DESCRIPTION OF THE PREFERRED EMBODIMENTS

Figure 1:
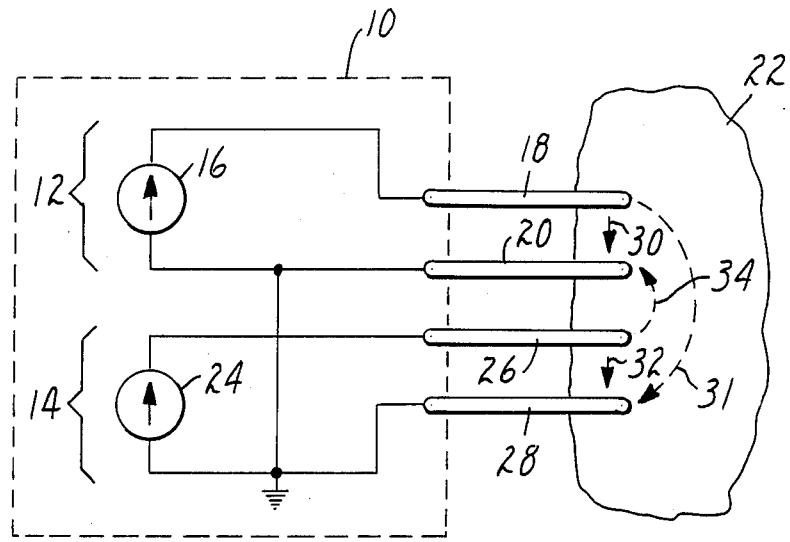
FIG. 1 illustrates a prior art, multichannel electrical stimulator.

FIG. 1 is illustrative of a prior art electrical stimulator 10. This electrical stimulator 10 is shown with two separate stimulation channels 12 and 14. Stimulation channel 12 has a current source 16 coupled to electrodes 18 and 20. Electrodes 18 and 20 serve as an electrode pair for stimulation channel 12. Electrode pair (18, 20) is adapted to be coupled to bodily tissue 22 which is to be stimulated by the electrical stimulator 10. Current source 16 supplies the desired amount of stimulating current for the stimulation channel 12 which is to be applied to the bodily tissue 22 via electrode pair 18, 20. Similarly, stimulation channel 14 has a current source 24 coupled to electrodes 26 and 28 which serve as the electrode pair for stimulation channel 14. Electrode pair 26, 28 is also adapted to be coupled to bodily tissue 22. Current source 16 and current source 24 have a common electrical ground. Current source 24 supplies the desired amount of stimulation current for stimulation channel 14 which is to be applied via electrode pair 26, 28 to bodily tissue 22. Shown for convenience in the diagram of FIG. 1, current source 16 contains an arrow indicating that the momentary current supplied by current source 16 is in the upward direction. Similarly, current source 24 also contains an upward arrow indicating the same instantaneous direction of current flowing in stimulation channel 14. It is to be recognized and understood, however, that the arrow in current sources 16 and 24 are for convenience and that current sources 16 and 24 may provide steady state alternating or other instantaneous current supply waveforms and may or may not be equal at any given instant of time. That is, current source 16 is completely independent from current source 24. Current source 16 supplies current to electrode 18. That current then is designed to theoretically pass through bodily tissue 22 and be returned to current source 16 from electrode 20. Similarly, for stimulation channel 14 current source 24 supplies current to electrode 26. In theory of operation, that current should pass through bodily tissue 22 and be returned to current source 24 from electrode 28.

In practice, it has been found that with electrical stimulator 10, that a portion of the current from current source 16 of channel 12 of electrical stimulator 10 passes from electrode 18 to electrode 20 as theoretically designed. This current is indicated by arrow 30. However, a portion of the current passing from electrode 18 may be diverted to electrode 28, since electrode 20 and electrode 28 are coupled to the same electrical ground. This current is indicated by arrow 31. For channel 14 of electrical stimulator 10, current from current source 24 passes from electrode 26 into bodily tissue 22. Now, however, there are two potential paths for that current to flow. A portion of the current will flow, as designed, directly to electrode 28 to be returned to current source 24. This current is illustrated in the diagram by arrow 32. However, in practice, electrode 20 competes for the current being supplied by electrode 26. Thus, some of the current supplied by electrode 26 does not pass to electrode 28 but rather is diverted, as illustrated by arrow 34, to electrode 20 instead. The result is a lack of isolation between channel 12 and channel 14 of electrical stimulator 10. Electrode 20 will receive more electrical current from bodily tissue 22 than desired while electrode 28 will receive less. The current illustrated by arrow 30 will be greater than designed while the current illustrated by arrow 32 will be less than designed. Thus, channel 14 of electrical stimulator 10 has an effect upon channel 12 of electrical stimulator 10. This results in application of electrical currents to bodily tissue 22 which are not as theoretically designed and, thus, the results achieved will be less than theoretially designed and the results achieved may be significantly impaired.

Figure 2:
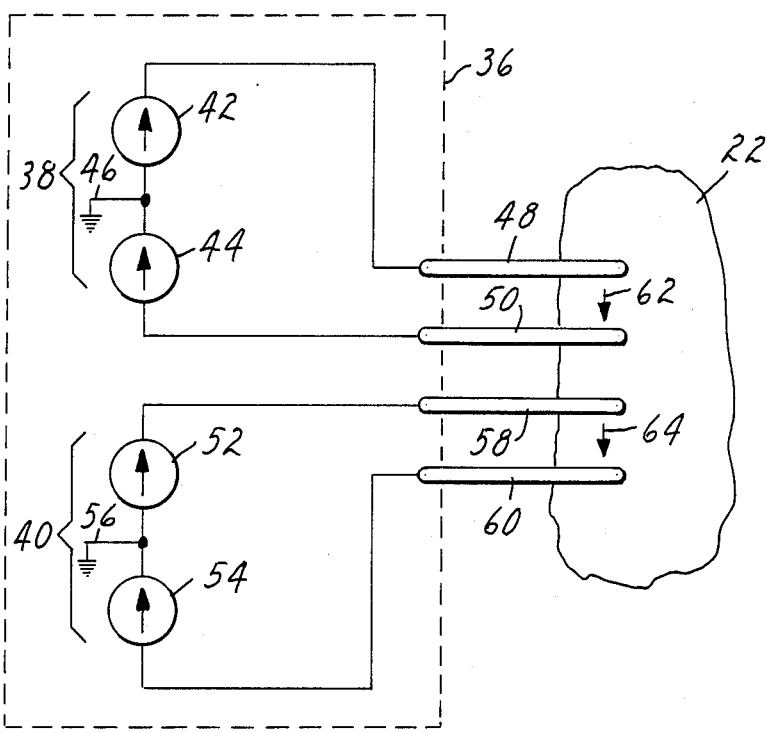
FIG. 2 is a diagram of an electrical stimulator of the present invention.

FIG. 2 illustrates one embodiment of the electrical stimulator 36 of the present invention. Electrical stimulator 36 also has two stimulation channels 38 and 40. Stimulation channel 38 has current source 42 and current source 44 coupled on either side of electrical common 46. Current source 42 is also coupled to electrode 48 while current source 44 is coupled to electrode 50. Electrode 48 and electrode 50 serve as the electrode pair for stimulation channel 38. Electrodes 48 and 50 are adapted to be coupled to bodily tissue 22 which is to be stimulated by the electrical stimulator 36. Similarly, stimulation channel 40 has current source 52 and current source 54 coupled on either side of electrical common 56. Current source 52 is also coupled to electrode 58 while current source 54 is also coupled to electrode 60. Electrodes 58 and 60 function as the electrode pair for stimulation channel 40. Electrodes 58 and 60 are adapted to be coupled to bodily tissue 22 which is to be stimulated by stimulation channel 40 of electrical stimulator 36.

Current source 42 and current source 44 are constructed to operate in concert with each other. At any given instant of time for stimulation channel 38, the current flowing through current source 42 should be substantially equal to the current flowing through current source 44. Similarly, for stimulation channel 40 current source 52 and current source 54 operate in concert. At any given instant in time for stimulation channel 40, the current flowing through current source 52 will be substantially equal to the current flowing through current source 54. That is, if current source 52 is sourcing a certain amount of current to electrode 58 then current source 54 will be arranged to sink that same certain amount of current from electrode 60. Current source 42 and current source 44 are arranged to operate on substantially identical currents. Similarly, current source 52 and current source 54 are arranged to operate on substantially identical currents. It is to be recognized and understood, however, that exact identicality between electronic circuits is extremely unlikely. Therefore, substantially identical currents refers to currents which are designed to be equal and are equal within the realm of reasonable circuit design constraints and practicality in component value variations.

With a current source associated with each electrode, the electrical stimulator 36 of FIG. 2 achieves a much greater channel isolation in its operation in conjunction with bodily tissue 22. Current source 42 sources (or sinks) a given amount of current to electrode 48. That same amount of current is sinked (or sourced) into electrode 50 by current source 44. Therefore, the current illustrated by arrow 62 represents the current sourced (or sinked) by current source 42 and the current sinked (or sourced) by current source 44. Similarly, for stimulation channel 40, electrode 58 sources (or sinks) the exact amount of current supplied by current source 52. Electrode 60 sinks (or sources) the exact amount of current determined by current source 54. Therefore, the current flowing between electrodes 58 and 60 represented in the diagram by arrow 64 is substantially that current determined by current source 52 and current source 54. The result is that electrical stimulator 36 has significantly greater isolation between stimulation channel 38 and stimulation channel 40. There is significantly less contamination of the current flowing in bodily tissue 22 between electrode pairs 58 and 60 due to the physical proximity of electrode pairs 48 and 50.

Figure 3:
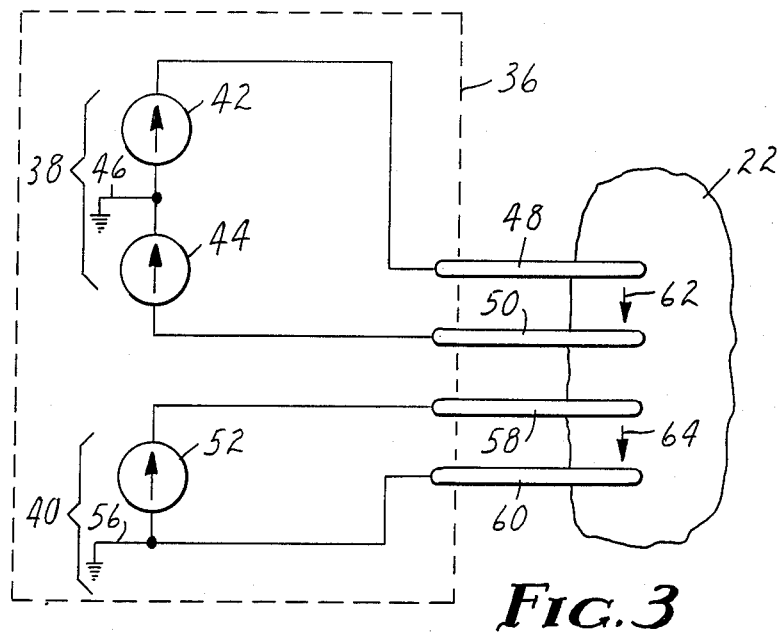
FIG. 3 is a diagram of an alternative embodiment of an electrical stimulator of the present invention.

FIG. 3 illustrates an alternative embodiment of the electrical stimulator 36. In this embodiment, stimulation channel 38 is identical to stimulation channel 38 of electrical stimulator 36 of FIG. 2. Again, current source 42 and current source 44 connected on either side of electrical common 46. Current source 42 is coupled to electrode 48 while current source 44 is coupled to electrode 50. Electrode 48 and electrode 50 are adapted to be coupled to bodily tissue 22 and produce current in bodily tissue 22 illustrated by arrow 62. Stimulation channel 40 in electrical stimulator 36 of FIG. 3 is similar to stimulation channel 40 of the electrical stimulator 36 of FIG. 2. Again, current source 52 is coupled on one side of electrical common 56 and is coupled to electrode 58. Electrode 58 and electrode 60 are adapted to be coupled to bodily tissue 22 to supply a stimulation current to bodily tissue 22 which is represented by arrow 64. The difference between stimulation channel 40 of FIG. 3 and stimulation channel 40 of FIG. 2 is that current source 54 is omitted in the embodiment illustrated in FIG. 3. Since the current sourced (or sinked) by electrode 48 is determined by current source 42 and since the current sinked (or sourced) by electrode 50 is determined by current source 44 and the current sourced (or sinked) by electrode 58 is determined by current source 52. The only current left to be sinked (or sourced) by electrode 60 is that remaining current. Since current sources 42 and 44 are balanced, the current sourced (or sinked) by electrode 48 equals the current sinked (or sourced) by electrode 50. The remaining current available to be sinked (or sourced) by electrode 60 is that current which is sourced (or sinked) by electrode 58 as determined by current source 52. Thus, one current source, namely current source 54, can be omitted from the diagram and the isolation between channel 38 and channel 40 may still be achieved.

Figure 4:
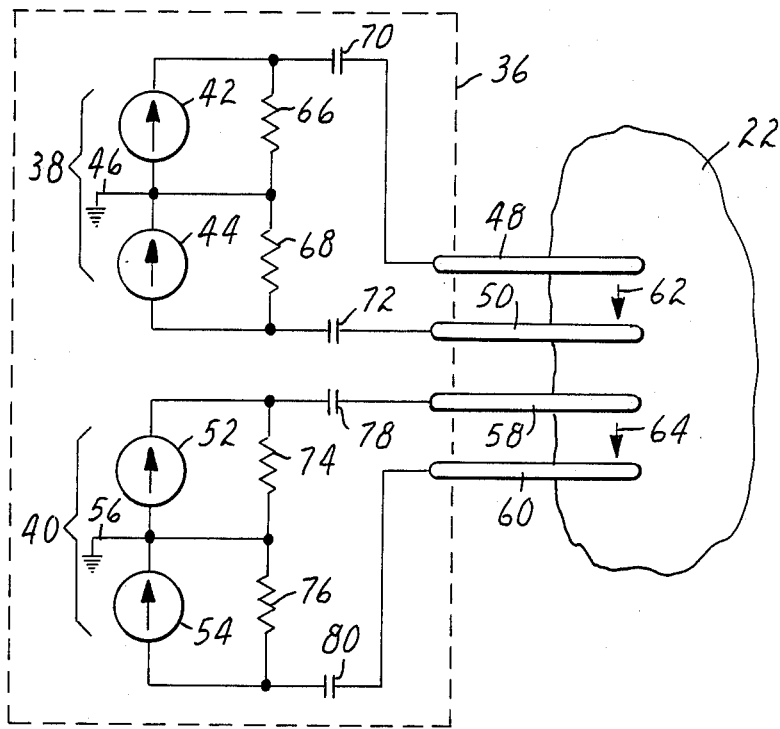
FIG. 4 is a diagram of an alternative embodiment of an electrical stimulator of the present invention.

FIG. 4 represents still another alternative embodiment of the electrical stimulator 36 of the present invention. In the electrical stimulator 36 illustrated in FIG. 4, both stimulation channel 38 and stimulation channel 40 have their outputs capacitively coupled to their respective electrode pairs 48, 50 and 58, 60. For stimulation channel 38, shunt resistances 66 and 68 serve to carry the difference in current between non-exactly matched current sources 42 and 44. Capacitors 70, coupled between current source 42 and electrode 48, and capacitor 72, coupled between current source 44 in electrode 50 serve to capacitively couple stimulation channel 38 to electrode pair 48, 50. Resistor 66 is coupled across current source 42 and resistor 68 is coupled across current source 44. Similarly, for stimulation channel 40, resistor 74 is coupled across current source 52 and resistor 76 is coupled across current source 44. Again, resistor 74 and 76 serve to take up the mismatch, if any, between current source 52 and current source 54. Capacitor 78, coupled between current source 52 and electrode 58 and capacitor 80, coupled between current source 54 and electrode 60, serve to capacitively couple stimulation channel 40 to electrode pair 58 and 60.

Figure 5:
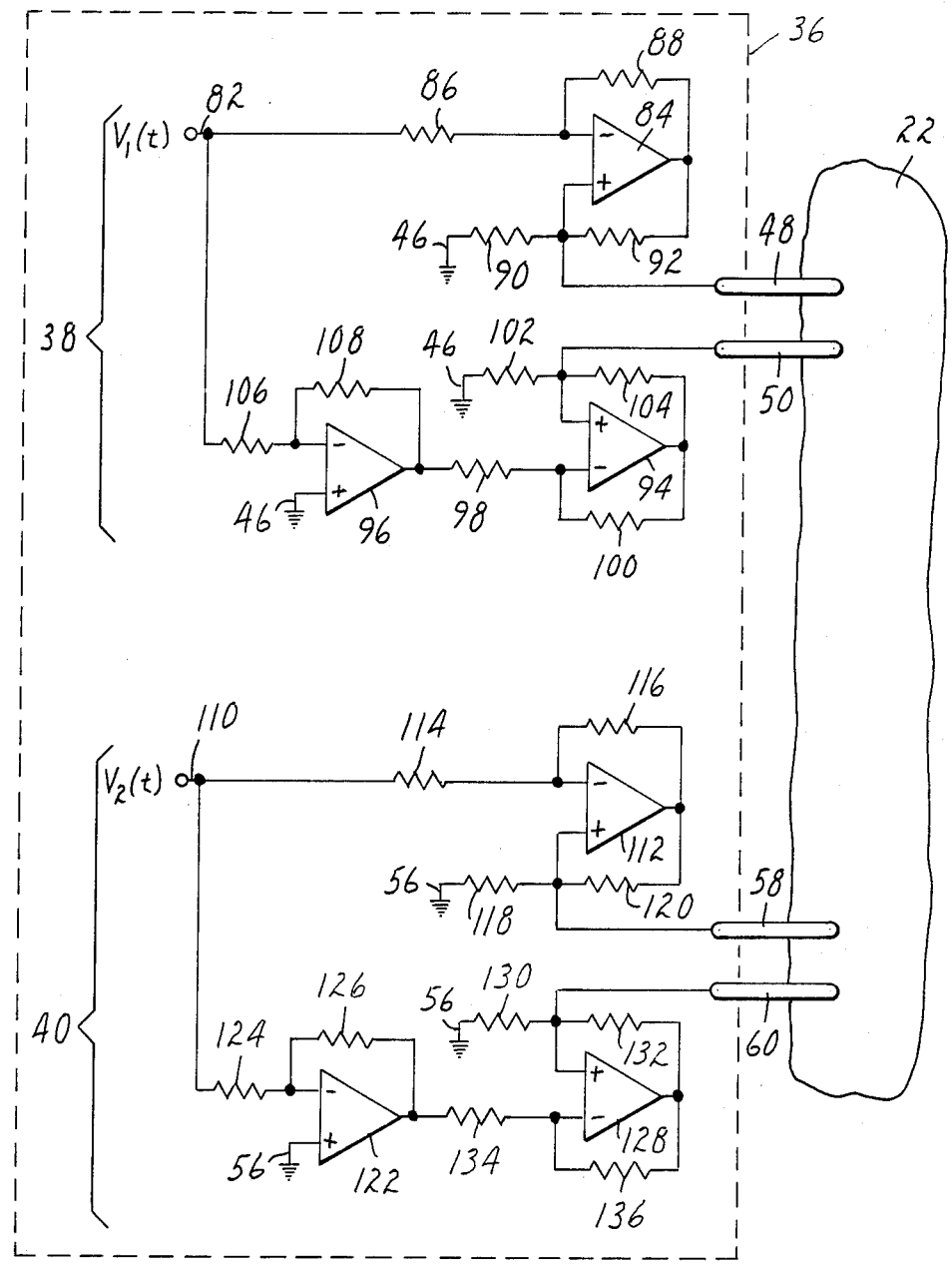
FIG. 5 is a detailed circuit diagram of an electrical stimulator of the present invention.

FIG. 5 illustrates a detailed circuit diagram of a preferred embodiment of electrical stimulator 36. Again, electrical stimulator 36 consists of stimulation channel 38 and stimulation channel 40. Stimulation channel 38 is adapted to be coupled to bodily tissue 22 with electrodes 48 and 50 while stimulation channel 40 is adapted to be coupled to bodily tissue 22 through electrodes 58 and electrode 60. Stimulation channel 38 is coupled to a voltage source at point 82. Operational amplifier 84 along with resistors 86, 88, 90 and 92 operate as current source 42. Resistor 86 is coupled between voltage source point 82 and the negative input to operational amplifier 84. Resistor 88 is coupled between the negative input to operational amplifier 84 and the output of operational amplifier 84. Resistor 92 is coupled between the positive input to operational amplifier 84 and the output of operational amplifier 84. Resistor 90 is coupled between the positive input to operational amplifier 84 and to electrical common 46. Positive input to operational amplifier 84 is also coupled to electrode 48. The values for resistors 86, 88, 90 and 92 can be determined by making the value of resistor 92 divided by the value of resistor 90 equal to the value of resistor 86 divided by the value of resistor 88. The magnitude of the current supplied by this current source will be roughly equal to the value of the voltage source from voltage point 82 divided by the value of resistor 90. Current source 44 in this diagram is shown schematically consisting of operational amplifier 94, operational amplifier 96, resistors 98, resistor 100, resistor 102, resistor 104, resistor 106 and resistor 108. Resistor 106 is coupled between voltage source point 82 and the negative input to operational amplifier 96. Operational amplifier 96 serves to invert the voltage appearing at voltage point 82 to enable operational amplifier 94 to generate a current equal and opposite to the current generated by operational amplifier 84. The positive input to operational amplifier 96 is coupled to electrical common 46. Resistor 108 is coupled between the negative input of operational amplifier 96 to the output of operational amplifier 96. Resistor 98 is coupled between the output of operational amplifier 96 and the negative input of operational amplifer 94. Resistor 100 is coupled between the negative input to operational amplifier 94 in the output of operational amplifer 94. Resistor 104 is coupled between the positive input to operational amplifier 94 and the output of operational amplifier 94. Resistor 102 is coupled between the positive input to operational amplifier 94 into electrical common. The positive input to operational amplifier 94 is also coupled to electrode 50.

The value of resistor 104 divided by the value of resistor 102 should equal the value of resistor 98 divided by the value of resistor 100. The magnitude of the current supplied by this current source is roughly equal to the value supplied by voltage point 82 divided by the value of resistor 102. The value of resistor 106 and the value of resistor 108 should also be equal. Operational amplifier 96 and resistors 106 and 108 serve to invert the voltage appearing at voltage point 82. The value of resistor 86 and value of resistor 98 should match as should the value of resistor 88 and the value of resistor 100, the value of resistor 90 and the value of resistor 102, and the value of resistor 92 and the value of resistor 104. Similarly, operational amplifier 84 and operational amplifier 94 should also be matched. In one preferred embodiment, operational amplifiers 84 and 94 are Model No. 741 operational amplifiers obtained from suppliers such as Texas Instruments and National Semiconductor. In a preferred embodiment, the voltage appearing at voltage point 82 would vary between -10 volts and +10 volts and the value of all resistors 86, 88, 90, 92, 98, 100, 102, 104, 106 and 108 would be 2 kilohms.

The electrical schematic for stimulation channel 40 is identical to that previously described for stimulation channel 38. Voltage point 110 serves to supply stimulation channel 40. Current source consisting of operational amplifiers 112, resistors 114, 116, 118 and 120 are coupled to electrode 58. Operational amplifier 122 resistors 124 and 126 serve to invert the voltage appearing at voltage point 110. The other current source consisting of operational amplifier 128 and resistors 130, 132, 134 and 136 are coupled to electrode 60. The same constraints or the values of these components of stimulation channel forty are identical to those constraints for stimulation channel 38. It is to be recognized and understood, however, that the component values between electrical stimulation channel 38 and electrical stimulation channel 40 may not be equal. The component values just need to be consistent within one of the stimulation channels 38 or 40. It is also to be recognized and understood, of course, that even if the component values between electrical stimulation channel 38 and electrical stimulation channel 40 are equal that the stimulation currents supplied by electrode pairs 48 and 50 and 58 and 60, respectively, at any given instant in time need not be identical. The stimulation current may be varied according to the voltage source appearing at voltage points 82 and 110, respectively.

Thus, there has been shown and described a novel electrical stimulator. It is to be recognized and understood, however, that various changes, substitutions and modifications in the form and the details of the described invention may be made by those skilled in the art without departing from the scope of the following claims.

What is claimed is:

1. An electrical stimulator having a plurality of channels having an electrical common, said stimulator adapted to stimulate tissue with an electrical current on each of said plurality of channels, comprising:
   a first electrode and a second electrode for each of said plurality of channels, said first electrode and said second electrode adapted to be coupled to said tissue for passing said electrical current through said tissue between said first electrode and said second electrode; and
   a first current source and a second current source for each of said plurality of channels, said first current source coupled between said electrical common and said first electrode and said second current source being coupled between said second electrode and said electrical common;
   means for operating said first current source and said second current source simultaneously for more than one of said plurality of channels;
   individually for each of said more than one of said plurality of channels, the current generated by said first current source being substantially equal in magnitude to the current generated by said second current source and being oppositely oriented at a given point in time;
   whereby better isolation of stimulus between said plurality of channels is achieved.

2. An electrical stimulator as in claim 1 in which said first current source and said second current source vary in magnitude and polarity.

3. An electrical stimulator having a plurality of channels having an electrical common with each adapted to simultaneously at stimulate tissue with an electrical current, comprising:
   an electrode pair for each of said plurality of channels, said electrode pair adapted to be coupled to said tissue for passing electrical current through said tissue between said electrode pair;

a pair of current sources for each of said plurality of channels, said pair of current sources connected positively and negatively, respectively, to electrical common and with said pair of current sources being individually operatively coupled to said electrode pair;

individually for each of said plurality of channels in a given instant of time, the current generated by said pair of current sources being substantially equal in magnitude and coupled in opposite directions with respect to said electrical common;

whereby each of said electrode pair sources and sinks substantially identical current to and from said tissue and a better isolation of stimulus between electrode pairs of different ones of said plurality of channels is achieved.

4. An electrical stimulator having a plurality of channels having an electrical common, said stimulator adapted to simultaneously stimulate tissue with an electrical current on each of said plurality of channels, comprising:

a first electrode and a second electrode for each of said plurality of channels, said first electrode and said second electrode adapted to be coupled to said tissue for passing said electrical current through said tissue between said first electrode and said second electrode;

a first current source and a second current source for all but one of said plurality of channels, said first current source coupled between said electrical common and said first electrode and said second current source being coupled between said second electrode and electrical common;

at a given point in time and for each of said all but one of said plurality of channels, the current generated by said first current source being substantially equal in magnitude to the current generated by said second current source and being oppositely oriented;

a current source for said one of said plurality of channels operating simultaneously with each of said all but one plurality of channels, and coupled between electrical common and said first electrode and said second electrode being coupled to electrical common;

whereby better isolation of stimulus between said plurality of channels is achieved.

* * * * *